United States Patent [19]

De'Ath et al.

[11] 4,331,678
[45] May 25, 1982

[54] CARBAMOYL PYRAZOLE COMPOUNDS AND THEIR PESTICIDAL APPLICATION

[75] Inventors: Norman J. De'Ath; John Gillon, both of Cambridge, England

[73] Assignee: FBC Limited, Hauxton, England

[21] Appl. No.: 111,985

[22] Filed: Jan. 14, 1980

[30] Foreign Application Priority Data

Jan. 18, 1979 [GB] United Kingdom ............... 7901889

[51] Int. Cl.³ .................... A01N 43/56; C07D 231/18
[52] U.S. Cl. ................................. 424/273 P; 548/377
[58] Field of Search .................... 548/377; 424/273 P

[56] References Cited

U.S. PATENT DOCUMENTS 4,008,249  2/1977  Fischer et al. ...................... 548/377

FOREIGN PATENT DOCUMENTS 850220   7/1977  Belgium .
7301203  7/1974  Netherlands .
7409433  1/1976  Netherlands .

OTHER PUBLICATIONS

Sandstrom, Chem. Abst. 1956, vol. 50, pp. 12029-12030.
Sandstrom, Chem. Abst. 1962, vol. 56, pp. 11593-11594.
Stachel, Chem. Abst. 1964, vol. 58, No. 4540c.
Beyer et al., Chem. Ber. 1959, vol. 92, pp. 2593-2599.

Primary Examiner—Henry R. Jiles
Assistant Examiner—Natalia Harkaway
Attorney, Agent, or Firm—Morgan, Finnegan, Pine, Foley & Lee

[57] ABSTRACT

Carbamoyl pyrazoles of formula

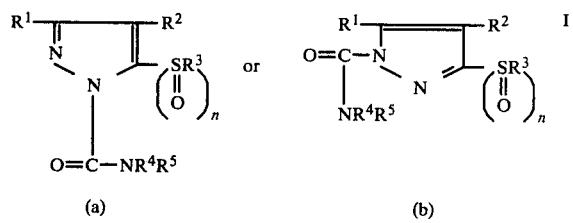

and their salts, wherein
$R^1$ represents alkyl or cycloalkyl;
$R^2$ represents a hydrogen atom or alkyl of 1-6 carbon atoms;
$R^3$ represents alkyl or alkenyl;
$R^4$ and $R^5$ are the same or different and each represents alkyl of 1-6 carbon atoms; and
n represents 0, 1 or 2,
are pesticides, especially insecticides.

12 Claims, No Drawings

CARBAMOYL PYRAZOLE COMPOUNDS AND THEIR PESTICIDAL APPLICATION

This invention relates to pesticidal compounds, their production, their compositions and their use.

Accordingly, the invention provides a compound which is a carbamoyl pyrazole of formula

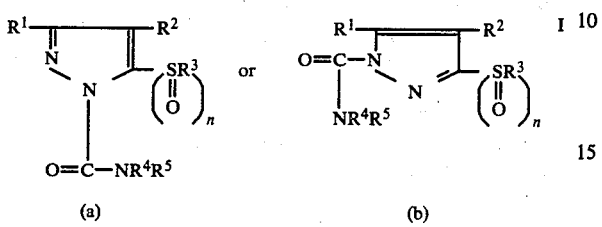

or a salt thereof, wherein $R^1$ represents alkyl or cycloalkyl;
$R^2$ represents a hydrogen atom or alkyl of 1-6 carbon atoms;
$R^3$ represents alkyl or alkenyl;
$R^4$ and $R^5$ are the same or different and each represents alkyl of 1-6 carbon atoms; and
n represents 0, 1 or 2.

The invention also provides a process for preparing the compound, which process comprises (a) reacting a pyrazole of formula

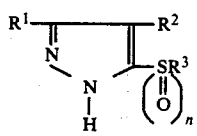

with a carbamoyl halide of formula $R^4R^5NCOX$ where X represents a halogen atom;

(b) reacting a carbonyl chloride of formula

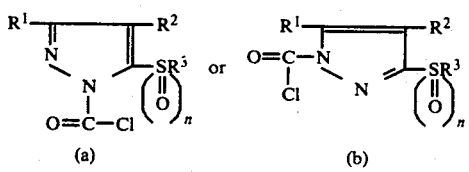

with an amine of formula $R^4R^5NH$;

(c) where n represents 1, oxidising the corresponding compound where n represents 0;

(d) where n represents 2, oxidising the corresponding compound where n represents 0 or 1;

(e) where the compound is a salt, salifying the corresponding carbamoyl pyrazole; or (f) where the compound is a carbamoyl pyrazole, desalifying a salt of the carbamoyl pyrazole.

The invention also provides a pesticidal composition containing the compound, especially such a composition comprising the compound together with at least one material selected from carriers, surface active agents, synergists, other pesticides and fertilizers.

The invention also provides a method of combating pests at a locus infested or liable to be infested with them, which method comprises applying to the locus a pest-combating amount of the compound.

Almost all the pyrazoles of formula II and their salts are novel. Accordingly, the invention provides the pyrazoles of formula II and their salts, excluding 3-methyl-5-(methylthio)pyrazole and its salts.

The invention also provides a process for preparing the novel pyrazoles of formula II and their salts, which process comprises (a) where n represents 0, reacting a ketone of formula

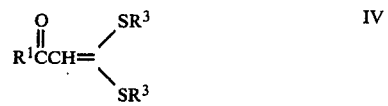

with hydrazine or a salt thereof, (b) where n represents 1 or 2, oxidising the corresponding compound of formula II where n represents 0; or (c) where n represents 2, oxidising the corresponding compound of formula II where n represents 1.

The invention also provides a process for preparing the pyrazoles of formula II where n represents 0 and their salts, which process comprises reacting a thione of formula

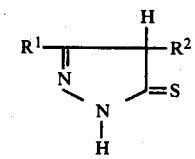

or a salt thereof, with a reactant of formula $R^3Y$ where Y represents a halogen atom or $\frac{1}{2}SO_4^{--}$.

The thione of formula V and its salts are novel, and the invention provides these per se.

The invention also provides a process for preparing the thione of formula V or a salt thereof, which process comprises (a) reacting a bis mercaptan of formula

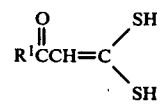

with hydrazine or a salt thereof; or (b) thiation of a pyrazolone of formula

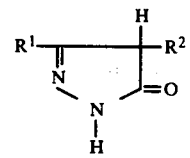

or a salt thereof.

The carbonyl chloride of formula III is also novel and the invention provides this per se.

The invention also provides a process for preparing the carbonyl chloride of formula III, which process comprises reacting the pyrazole of formula II or a salt thereof with phosgene.

The carbamoyl pyrazole of formula I, the pyrazole of formula II and the thione of formula V form salts. Salts may be formed with acids such as mineral acids, e.g. hydrochloric acid. Salts may be prepared from the non-salt form (i.e. the non-salt form may be salified), and the non-salt form may be prepared from the salts (i.e. the salts may be desalified), by ways which are conventional in themselves. Salts may be prepared by reacting the non-salt form with acids. The non-salt form may be prepared by reacting an acid salt with a base e.g. sodium hydroxide. Salts, however, are not preferred.

As can be seen from formulae I(a) and I(b) above, the

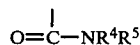

group can be on either nitrogen atom of the pyrazole ring. Preferably, however the compound is prepared, it has that structure possessed when prepared by process (a) above. When that process produces a single isomer, this is the preferred isomeric form. Usually, e.g. when $R^1$ contains 3 or more carbon atoms, only a single isomer is produced, which is believed to be of structure (a). Sometimes, e.g. when $R^1$ represents methyl, both isomers are produced, in which case they are both preferred. For convenience, the compounds are named in this specification as through they have structure (a).

Analogous considerations apply to the carbonyl chloride of formula III. Preferably, however the compound is prepared, it has that structure possess when prepared by the process described herein.

The production of the present compound by reacting the pyrazole of formula II with the carbamoyl halide of formula $R^4R^5NCOX$ is preferably carried out in the presence of a base, e.g. an inorganic or tertiary organic base (e.g. sodium carbonate, potassium carbonate or sodium hydride). X usually represents a chlorine atom. The reaction can advantageously be carried out in the presence of pyridine which serves as the base and also as a solvent. The reaction is preferably carried out at 15°–140° C.

The production of the present compound by reacting the carbonyl chloride of formula III with an amine is preferably carried out in the presence of a base, which may be an inorganic base (e.g. sodium carbonate) or an organic base (which may be excess of the reacting amine or may be for example a tertiary amine such as triethylamine). The reaction is usually carried out at a temperature from $-20°$ to $100°$ C., e.g. from $-20°$ to $80°$, preferably at ambient temperature.

When n represents 1, the present compounds have the group

at the 5-position. When n represents 2, the present compounds have the group

at the 5-position. The compounds where n represents 1 or 2 may be prepared by oxidising the corresponding compound where n represents 0, or, in the case where n represents 2, oxidising the corresponding compound where n represents 1. As oxidising agent there may be used, for example, hydrogen peroxide or sodium periodate. The stronger oxidising agents, e.g. hydrogen peroxide, may be used to convert a compound where n represents 0 to the corresponding compound where n represents 2. The weaker oxidising agents, e.g. sodium periodate, may be used to convert a compound where n represents 0 to the corresponding compound where n represents 1.

In the production of the novel pyrazoles of formula II and their salts, where n represents 0, by reacting $R^1COCH=C(SR^3)_2$ with hydrazine or a salt thereof, the hydrazine is conveniently added as hydrazine hydrate, $N_2H_4.H_2O$. The hydrazine may be added as a salt e.g. its hydrochloride or sulphate, but hydrazine salts are not preferred.

In the production of the pyrazole of formula II where n represents 1 or 2, or a salt thereof, by oxidising the corresponding compound of formula II wherein n represents 0, or, in the case where n represents 2, oxidising the corresponding compound where n represents 1, the oxidising agent may be, for example, hydrogen peroxide or sodium periodate.

The production of the pyrazole of formula II where n represents 0 or a salt thereof by reacting the thione of formula V with $R^3Y$ is usually carried out in the presence of a strong base such as sodium hydride. A suitable solvent is glyme (1,2-dimethoxyethane). The reaction is usually carried out at a temperature of 20°–100° C. Y usually represents a halogen atom e.g. chlorine.

In the production of the thione of formula V or a salt thereof by reacting the bis mercaptan of formula VI with hydrazine or a salt thereof, the hydrazine is conveniently added as hydrazine hydrate, $N_2H_4.H_2O$. The hydrazine may be added as a salt, e.g. its hydrochloride or sulphate, but hydrazine salts are not preferred.

The production of the thione of formula V by thiation of a pyrazolone of formula VII or a salt thereof may be carried out by means for instance of $P_2S_5$. The reaction may be carried out in a solvent such as pyridine. The reaction may be carried out at a temperature for instance of 50°–120° C.

The production of the carbonyl chloride of formula III by reacting the pyrazole of formula II or, less desirably, a salt thereof, with phosgene is preferably carried out in the presence of a weak tertiary base (e.g. dimethylaniline). The reaction is usually carried out at a temperature from $-30°$ to $20°$ C., preferably from $-30°$ to $0°$ C.

The present processes are usually conducted in the presence of a solvent, and usually are carried out at a temperature from $-30°$ to $150°$ C., e.g. 0°–150° C. The pressure may be for instance 0.5 to 10 atmospheres, conveniently ambient pressure.

The alkyl group which $R^1$ or $R^3$ may represent is preferably of 1–15, especially 1–6, carbon atoms, e.g. methyl, ethyl, isopropyl or t-butyl. $R^1$ preferably represents branched chain alkyl especially t-butyl. $R^3$ preferably represents methyl.

The cycloalkyl group which $R^1$ may represent is preferably of 3–6 carbon atoms, e.g. cyclopropyl.

The alkyl group of 1–6 carbon atoms which $R^2$, $R^4$ or $R^5$ may represent can be for instance methyl or ethyl, especially methyl.

The alkenyl group which $R^3$ may represent is preferably of 2–6 carbon atoms e.g. allyl.

In a preferred embodiment, $R^1$ represents alkyl of 1–15 carbon atoms or cycloalkyl of 3–6 carbon atoms; and $R^3$ represents alkyl of 1–15 carbon atoms or alkenyl of 2–6 carbon atoms. In a particular embodiment within this group, $R^1$ represents alkyl of 1–15 carbon atoms and n represents 0.

Particularly preferred are the compounds wherein
$R^1$ represents methyl, isopropyl, t-butyl or cyclopropyl;
$R^2$ represents a hydrogen atom;
$R^3$ represents methyl, ethyl or allyl; and
$R^4$ and $R^5$ each represents methyl or each represents ethyl.

A preferred particular compound is 3-t-butyl-1-(dimethylcarbamoyl)-5-(methylthio)pyrazole or a salt thereof.

The present compounds are pesticides. The compounds are particularly useful as insecticides. They are also acaricides and nematocides.

The compounds are preferably applied to a locus at which a crop is growing or is to grow, e.g. to combat insects thereon.

The present compounds are normally employed in the form of compositions, which can be prepared by admixing the ingredients. Usually the compositions are initially produced in the form of concentrates, e.g. containing 0.5–85% of the present compound, and these are diluted with water or hydrocarbon, usually water, for application, generally such that the concentration of the compound is 0.05–5%, though in ultra low volume application the concentration may be higher, e.g. up to 20%. Percentages, ratios and parts in this specification are by weight unless otherwise indicated.

The compositions normally contain a surface active agent and/or a carrier.

The carrier may be a liquid, e.g. water (e.g. water used to dilute a concentrate for application). If water is employed as carrier in a concentrate, an organic solvent may also be present as carrier, though this is not usually employed. A surface active agent may advantageously be present.

The carrier may be a liquid other than water, for example an organic solvent, such as a water immiscible solvent, e.g. a hydrocarbon which boils within the range 130°–270° C., in which the compound is dissolved or suspended. A concentrate containing a water immiscible solvent suitably also contains a surface-active agent so that the concentrate acts as a self-emulsifiable oil on admixture with water. The liquid may be a water-miscible solvent e.g. 2-methoxyethanol, methanol, propylene glycol, diethylene glycol, diethylene glycol monoethyl ether, formamide or methylformamide.

The carrier may be a solid, which may be finely divided. Examples of suitable solids are limestone, clays, sand, mica, chalk, attapulgite, diatomite, perlite, sepiolite, silicas, silicates, lignosulphonates, peat and solid fertilizers. The carrier can be of natural or synthetic origin or can be a modified natural material.

Wettable powders soluble or dispersable in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorodifluoromethane, and suitably also with a solvent.

A flowable suspension concentrate may be formed if the compound has a low water solubility by grinding the compound with water, a wetting agent and a suspending agent.

A flowable suspension concentrate wherein the carrier is a hydrocarbon which boils within the range 130°–270° C. rather than water may be formed.

Thus the present composition can for example be solid (e.g. a wettable powder or a granule) and contain a solid carrier, or liquid (e.g. an emulsifiable concentrate) and contain a liquid carrier which is a hydrocarbon which boils within the range 130°–270° C.

The term 'surface-active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with fatty alcohol ethoxylates or with alkylphenol ethoxylates, salts of such esters, fatty alcohol sulphates such as sodium dodecyl sulphate, sodium octadecyl sulphate or sodium cetyl sulphate, ethoxylated fatty alcohol sulphates, ethoxylated alkylphenol sulphates, lignin sulphonates, petroleum sulphonates, alkyl-aryl sulphonates such as alkyl-benzene sulphonates or lower alkylnaphthalene sulphonates, e.g. butylnaphthalene sulphonate, salts of sulphonated naphthalene-formaldehyde condensates, salts of sulphonated phenol-formaldehyde condensates, or more complex sulphonates such as the amide sulphonates e.g. the sulphonated condensation product of oleic acid and N-methyl taurine or the dialkyl sulphosuccinates e.g. the sodium sulphonate of dioctyl succinate.

The surface active agents may also comprise nonionic agents, for example condensation products of fatty acid esters, fatty alcohols, fatty acid amides or fatty-, alkyl- or alkenyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethylammonium bromide or ethoxylated tertiary fatty amines.

Preferred surface active agents include ethoxylated fatty alcohol sulphates, lignin sulphonates, alkyl-aryl sulphonates, salts of sulphonated naphthalene-formaldehyde condensates, salts of sulphonated phenol-formaldehyde condensates, dialkyl sulphosuccinates, alkylphenol ethoxylates, and fatty alkyl ethoxylates.

Non-ionic surface active agents are preferred.

The present compound, e.g. 3-t-butyl-1-(dimethylcarbamoyl)-5-(methylthio)pyrazole, may be used in admixture or sequence with another pesticide, especially a fungicide or another insecticide or acaricide. The invention provides a one pack presentation, in which the present compound is already mixed with other pesticide, and also a single package designed to hold the present compound and other pesticide in separate containers, for mixing, e.g. in a spray tank, for application.

The other pesticide may be one or more specified in the Pesticide Manual, fifth edition, edited by Martin & Worthing, issued by the British Crop Protection Council.

The other insecticide or acaricide may be for instance one or more of demeton-S-methyl (S-2-ethylthioethyl 0,0-dimethyl phosphorothioate), dimethoate (0,0- dimethyl S-methylcarbamoylmethyl phosphorodithioate), formothion (S-[N-formyl-N-methylcarbamoylmethyl] 0,0-dimethyl phosphorodithioate), oxydemeton-methyl (S-2-ethylsulphinylethyl 0,0-dimethyl phosphorothioate), pirimicarb (2-dimethylamino-5,6-dimethylpyrimidin-4-yl dimethylcarbamate), thiometon (S-2-ethylthioethyl, 0,0-dimethyl phosphorodithioate), BHC (benzene hexachloride), aldrin (1,2,3,4,10,10-hexachloro-1,4a5,8,8a-hexahydro-exo-1,4-endo-5,8-dimethanonaphthalene), fenitrothion (0,0-dimethyl 0-4-nitrom-tolyl phosphorothioate), omethoate (0,0-dimethyl S-methylcarbamoylmethyl phosphorothioate), pirimiphos-methyl (0-2-diethylamino-6-methyl-pyrimidin-4-yl 0,0-dimethyl phosphorothioate), DDT (1,1,1-trichloro-2,2-di[chlorophenyl]ethane), aldicarb (2-methyl-2-(methylthio)propionaldehyde 0-methylcarbamoyloxime), oxamyl (S-methyl N',N'-dimethyl-N-(methylcarbamoyloxy)-1-thiooximidate), chlorfenvinphos (2-chloro-1-(2,4-dichlorophenyl)vinyldiethyl phosphate), amitraz (2-methyl-1,3-di-(2,4-xylylimino)-2-arzapropane), cyhexatin (tricylcohexyltin hydroxide), dicofol (2,2,2-trichloro-1,1-di-(4-chlorophenyl)ethanol), bendiocarb (2,2-dimethyl-1,3-benzodioxol-4-yl methylcarbamate), binapacryl (2-sec-butyl-4,6-dinitrophenyl 3-methylcrotonate), bromopropylate (isopropyl 4,4'-dibromobenzilate), thiofanox (3,3-dimethyl-1-(methylthio)butanone 0-methylcarbamoyloxime), terbufos (S-tert-butylthiomethyl 0,0-diethyl phosphorodithioate), phorate (0,0-diethyl S-ethylthiomethyl phosporodithioate), carbaryl (1-naphthyl methylcarbamate), chlormephos (S-chloromethyl 0,0-diethyl phosphorodithioate), chloropropylate (isopropyl 4,4'-dichlorobenzilate), chlorpyrifos (0,0-diethyl 0-3,5,6-trichloro-2-pyridyl phosphorothioate), a synthetic pyrethroid e.g. decamethrin ((S)-α-cyano-3-phenoxybenzyl cis (1R,3R)-3-(2,2-dibromovinyl)-2,2-dimethylcyclopropanecarboxylate), permethrin (3-phenoxybenzyl (+)-cis,trans-3-(2,2-dichlorovinyl)-2,2-dimethylcyclopropanecarboxylate), fenvalerate (α-cyano-3-phenoxybenzyl-2(4-chlorophenyl)-3-methylbutyrate) or cypermethrin ((R,S)α-cyano-3-phenoxybenzyl (1R,1S)-cis,trans-3-(2,2-dichlorovinyl)-2,2-dimethylcyclopropanecarboxylate), dichlorvos (2,2-dichlorovinyl dimethyl phosphate), disulfoton (0,0-diethyl S-2-ethylthioethyl phosphorodithioate), carbofuran (2,3-dihydro-2,2-dimethylbenzofuran-7-yl methylcarbamate), endosulfan (6,7,8,9,10,10-hexachloro-1,5,5a,6,9,9a-hexahydro-6,9-methano-2,4,3-benzodioxathiepin 3-oxide), formetanate (3-dimethylaminomethyleneiminophenyl methylcarbamate) iodofenphos (0-2,5-dichloro-4-iodophenyl 0,0-dimethyl phosphorothioate), methamidophos (O,S-dimethylphosphoramidothioate), methiocarb (4-methylthio-3,5-xylyl methylcarbamate), methomyl (S-methyl N-(methylcarbamoyloxy)thioacetamidate), propargite (2-(4-tert-butylphenoxy)cyclohexyl prop-2-ynyl sulphite), quinalphos (0,0-diethyl 0-quinoxalin-2-yl phosphorothioate), tetrachlorvinphos (2-chloro-1-(2,4,5-trichlorophenyl)ethenyl dimethyl phosphate), tetradifon (4-chlorophenyl 2,4,5-trichlorophenyl sulphone) and trichlorphon (dimethyl 2,2,2-trichloro-1-hydroxyethylphonate).

In a particular embodiment 3-t-butyl-1-(dimethylcarbamoyl)-5-(methylthio)pyrazole is used in admixture or sequence with bendiocarb.

The ratio of the present compound to the other pesticide may vary over a wide range according to the particular compounds involved and the intended use. In general, the ratio of present compound to other pesticide lies in the range 1:0.1 to 1:15.

The present compounds may be in admixture with a synergist, e.g. piperonyl butoxide (5-(2-[2-butoxyethoxy]ethoxymethyl)-6-propyl-1,3-benzodioxole).

The compounds may be in admixture with non-phytotoxic oils, e.g. Agri-Oil Plus, Sun Oil 11E or Fyzol 11E.

The compounds may be in admixture with fertilizers.

In use, the compounds are generally applied at a rate of 0.1–10 kg per hectare.

To combat pests at a locus where plants are growing or are to grow, the compounds may be applied for example at a rate of 0.1–4 kg per hectare.

To combat pests which are a public health nuisance, e.g. houseflies or cockroaches, the compounds may be applied to surfaces, for instance at a rate of 100–3000 mg per square meter, or into the atmosphere, for instance at a rate of 0.3–30 mg per cubic meter.

The present compounds may be applied for instance to plants (including seeds), the soil (including compost), land or aquatic areas, animals, or to building or furniture surfaces. The plants can be a plantation crop, an ornamental crop or a food crop, e.g. a vegetable or fruit crop. Preferred crops include sugar beet, potatoes, beans, brassicas (e.g. cauliflowers or Brussels sprouts), rice, carrots, cotton, tobacco, citrus fruit, peaches, olives and grapes. The compounds are preferably used as insecticides, e.g. for application to a locus at which a crop e.g. a food crop is growing or, less preferably, is to grow.

The compounds are active against arthropods. The compounds are active against a wide range of insects e.g. *Musca domestica*, cockroaches e.g. *Blattella germanica*, and especially Hemiptera e.g. aphids, scale insects, mealy bugs, leaf and plant hoppers (e.g. rice hoppers), whiteflies and plant bugs. The compounds are active for instance against *Megoura viciae, Myzus persicae, Aphis fabae, Brevicoryne brassicae, Cavariella aegopodii* and *Hyalopterus amygdali*, wireworms (e.g. *Agriotes* spp), Cabbage root fly (*Erioischia brassicae*) and caterpillars (e.g. *Pieris rapae* or *Pieris brassicae*). The compounds show systemic activity in plants, e.g. sugar beet or Brussels sprouts, and also contact activity.

The invention is illustrated by the following Examples, in which temperatures are in degrees Centigrade.

EXAMPLE 1

4,4-Dimethyl-1,1-bis(methylthio)-1-penten-3-one

To a slurry of sodium hydride (19.2 g) in dry benzene (250 ml), was added all at once with stirring, pinacolone (20 g, 25 ml). After a few minutes stirring, carbon disulphide (15.5 g, 12.5 ml) was added dropwise. The reaction mixture was cooled to 15°, and dimethyl formamide (150 ml) was added dropwise with stirring and cooling over half an hour. The reaction mixture was stirred for a further ½ hour, and then warmed to 30°, giving a dark orange solution. After cooling to 15°, the solution was treated dropwise with methyl iodide (56.8 g, 25 ml), and was then stirred overnight. The solution was then refluxed for ½ hour, allowed to cool, diluted with benzene (200 ml) and pitched into iced water (1 liter). The organic layer was separated, washed with water (2×100 ml), dried and evaporated. The residue was distilled in vacuo to give the title compound (15 g, 36% yield), boiling point 78°–104° at 0.3 mm.

EXAMPLE 2

3-t-Butyl-5-(methylthio)pyrazole

Hydrazine hydrate (4 g, 3.9 ml) was added dropwise to a cooled solution of the product of Example 1 (15 g) in ethanol (75 ml). The reaction mixture was refluxed until evolution of methyl mercaptan ceased (2 hours), and allowed to cool. Most of the ethanol was evaporated off, and the residue was pitched into water, and ether extracted. The ethereal solution was dried over magnesium sulphate, and evaporated to give a pale yellow solid, which was recrystallised from 1:1 benzene/60°–80° petrol to give 3-t-butyl-5-(methylthio)-pyrazole, 6.0 g, (48% yield), melting point 142°–4°.

EXAMPLE 3

3-t-Butyl-1-(dimethylcarbamoyl)-5-(methylthio)-pyrazole

A mixture of 3-t-butyl-5-methylthiopyrazole (6.0 g) and dimethylcarbamoyl chloride (4.3 g) in pyridine (40 ml) were refluxed (at 115° C.) for 16 hours. The pyridine was evaporated, and the residue poured into water and extracted with chloroform. The chloroform layer was washed with 2 N HCl (2×50 ml), then water (50 ml), dried and evaporated to give an oil which soon crystallised. Recrystallisation from 60°–80° petrol at 0° C. gave 5.0 g of 3-t-butyl-1-(dimethylcarbamoyl)-5-(methylthio)pyrazole (59% yield), melting point 56°–8°. Only a single isomer was shown to be present by nuclear magnetic resonance spectroscopy (NMR) and thin layer chromatography.

Analysis: Found: C, 54.78%; H, 8.05%; N, 16.97%; $C_{11}H_{19}N_3OS$ requires: C, 54.74%; H, 7.94%; N, 17.41%;:

EXAMPLE 4–8

In a similar way to Examples 1–3, the following carbamoyl pyrazoles of formula I in which $R^2$ represents a hydrogen atom, $R^4$ and $R^5$ each represents methyl and n represents O were prepared. They were obtained as oils.

| Ex. | $R^1$ | $R^3$ | Analysis | |
|---|---|---|---|---|
| 4 | methyl | methyl | Found: $C_8H_{13}N_3OS$ requires: | C, 48.1; H, 6.75; N, 21.15% <br> C, 48.22; H, 6.58; N, 21.09% |
| 5 | cyclopropyl | methyl | Found: $C_{10}H_{15}N_3OS$ requires: | C, 51.95; H, 6.84; N, 16.3% <br> C, 53.31; H, 6.71; N, 18.65% |
| 6 | isopropyl | methyl | Found: $C_{10}H_{17}N_3OS$ requires: | C, 53.19; H, 7.26; N, 17.99% <br> C, 52.83; H, 7.54; N, 18.49% |
| 7 | t-butyl | ethyl | Found: $C_{12}H_{21}N_3OS$ requires: | C, 56.8; H, 8.5; N, 16.96% <br> C, 56.44; H, 8.29; N, 16.46% |
| 8 | cyclopropyl | ethyl | Found: $C_{11}H_{17}N_3OS$ requires: | C, 55.6; H, 7.3; N, 18.02% <br> C, 55.2; H, 7.16; N, 17.56% |

In the case of Example 4, the product contained two isomers by NMR, in the case of the other Examples only one.

The yields were as follows: Example 4: 58%; Example 5: 83%; Example 6: 82%; Example 7: 87%; and Example 8: 68%.

EXAMPLE 9

Dimethylcarbamoyl chloride (10.7 g, 9.1 ml) was added to a solution of 3-t-butyl-5-(methylthio)pyrazole (17.0 g) and pyridine (8 ml) in benzene (100 ml). The reaction mixture was refluxed (at 80°) for 24 hours, allowed to cool, and washed with water (50 ml), 2 N HCl, (25 ml) and water again (50 ml). The organic layer was dried, and evaporated to give an oil which soon crystallised. Recrystallisation from petrol afforded 1-(dimethylcarbamoyl)-3-t-butyl-5-(methylthio)pyrazole, 15.1 g, 62% yield, of melting point 58°–60°.

EXAMPLE 10

Example 9 was repeated but using xylene as solvent and refluxing (at 140°) for 12 hours, to give a 58% yield of the same product, melting point 57°–9°.

EXAMPLE 11

To a slurry of 3-t-butylpyrazole-5-thiol (10 g) in dry dimethoxyethane (100 ml) was added portionwise, with stirring, sodium hydride (1.6 g). Stirring at room temperature was continued for a few minutes, and then allyl bromide (7.8 g) was added. The reaction mixture was stirred for 2 hours, filtered, and evaporated. The residue was dissolved in ether and washed with water, and the ether layer separated, dried, and evaporated to give 3-t-butyl-5-(allylthio)pyrazole, as a pale brown oil (11.0 g), 88% yield.

EXAMPLE 12

The product of Example 11 (5.0 g) was dissolved in dry dimethoxyethane (75 ml), and sodium hydride (0.67 g) added in small portions, with stirring and ice cooling. After stirring the mixture for 15 minutes at room temperature, dimethylcarbamoyl chloride (3.0 g) was added dropwise. Stirring was continued for 1½ hours at room temperature, and the reaction mixture was then pitched into iced water, ether extracted and worked up to give 1-(dimethylcarbamoyl)-3-t-butyl-5-(allylthio)-pyrazole, 4.8 g, 70% yield.

Analysis:

|  | $C_{13}$ | $H_{21}$ | $N_3$ |
|---|---|---|---|
| Theory: | 58.39 | 7.92 | 15.72 |
| Found: | 58.42 | 7.51 | 15.83 |

NMR showed only a single isomer to be present.

EXAMPLE 13

A solution of 3-t-butyl-5-(methylthio)pyrazole (10 g), and triethylamine (6.0 g) were added dropwise at −20° to a stirred solution of phosgene (7.5 ml) in tetrahydrofuran (75 ml). The solution was allowed to come to room temperature, and was then stirred for 2 hours. Excess phosgene was removed by drawing dry air through the mixture for ½ hour. The reaction mixture was filtered, and evaporated to give a yellow oil which quickly crystallised. Recrystallisation from petrol gave 3-tert-butyl-1-chlorocarbonyl-5-(methylthio)pyrazole, 5.0 g (64% yield), melting point 64°–6°.

EXAMPLE 14

3-t-butyl-1-chlorocarbonyl-5-(methylthio)pyrazole (4.0 g) in ether (25 ml) was added dropwise with stirring to a solution of diethylamine (3.9 g, 5.5 ml) in ether (25 ml) at room temperature. The reaction mixture was refluxed for ½ hour and then filtered, and the ether layer washed with water, dried and evaporated to give crude product. Recrystallisation from petrol gave 1-(diethylcarbamoyl)-3-t-butyl-5-(methylthio)pyrazole, melting point 55°–6°. Yield 54%.

EXAMPLE 15

Gaseous dimethylamine was bubbled into a stirred, cooled (−20°) solution of 1-chlorocarbonyl-3-tert-butyl-5-(methylthio)pyrazole (23 g), in ether (400 ml) for 2 hours. The reaction mixture was allowed to come to room temperature with stirring, filtered, and the ethanol solution washed with water (100 ml), dried over anhydrous sodium sulphate, and evaporated to give 3-t-butyl-1-(dimethylcarbamoyl)-5-(methylthio)-pyrazole. Recrystallisation from petrol gave the pure compound (20.5 g, 83% yield), of melting point 56°–8°.

EXAMPLE 16

To a stirred solution of 1-chlorocarbonyl-3-tert-butyl-5-(methylthio)pyrazole (23 g) in benzene (200 ml) at room temperature was added dropwise diethylamine (16 g, 23 ml). A white precipitate formed rapidly. The reaction mixture was refluxed (at 80°) for two hours, allowed to cool, and water (100 ml) added. The organic layer was washed once again with water, separated, dried and evaporated to give 1-(diethylcarbamoyl)-3-t-butyl-5-(methylthio)pyrazole. Recrystallisation from petrol gave the pure compound (16.5 g, 59% yield), of melting point 55°–6°.

EXAMPLE 17

To a stirred, cooled, solution of 3-t-butyl-1-(dimethylcarbamoyl)-5-(methylthio)pyrazole (2.4 g) in methanol (50 ml) was added dropwise a solution of sodium periodate (2.2 g) in water (25 ml). The mixture was stirred overnight, when a heavy precipitate of sodium iodate formed. Filtration, evaporation, and ether extraction afforded 3-t-butyl-1-(dimethylcarbamoyl)-5-(methylsulphinyl)pyrazole, 1.3 g, of melting point 95°–6°.
Analysis:

|         | $C_{11}$ | $H_{19}$ | $N_3$ |
|---------|-------|-------|-------|
| Theory: | 51.34 | 7.44  | 16.33 |
| Found:  | 51.06 | 7.42  | 16.45 |

EXAMPLE 18

3-t-butyl-1-(dimethylcarbamoyl)-5-(methylthio)-pyrazole was dissolved in glacial acetic acid (10 ml) and 30% hydrogen peroxide (10 ml) added dropwise with stirring and cooling. The reaction mixture was stirred for 2 days at room temperature, when a white solid crystallised. The reaction mixture was pitched into ice/water, filtered and the white solid dried. Recrystallisation from hexane afforded 3-t-butyl-1-(dimethylcarbamoyl)-5-(methylsulphonyl)pyrazole, 0.6 g, of melting point 126°–8°. Its structure was confirmed by NMR.

EXAMPLE 19

To a stirred solution of 4,4-dimethyl-1,1-bis(methylthio)-1-penten-3-one (18.4 g) in ethanol, was added dropwise with stirring hydrazine hydrate (5.3 g), keeping the temperature below 25°. The reaction mixture was stirred briefly at room temperature, then refluxed for 2 hours. Evaporation of the solvent, and trituration with ether, afforded 3-t-butylpyrazole-5-thione (7.8 g, 20% yield), of melting point 147°–8°.

EXAMPLE 20

To a stirred solution of 3-t-butylpyrazole-5-thione (2.0 g) in glyme (50 ml) was added sodium hydride (0.6 g) in small quantities, with cooling. After stirring the mixture briefly at room temperature, iodomethane (1.85 g, 0.9 ml) was added. The reaction mixture was stirred at room temperature, then the solvent evaporated in vacuo. The residue was extracted with ether and washed with water to give after evaporation, 3-t-butyl-5-(methylthio)pyrazole (0.8 g, 36% yield), of melting point 135°–6° (after recrystallisation from petrol). The product was identical, by nuclear magnetic resonance spectroscopy, to that of Example 2.

EXAMPLE 21

Aqueous acetone solutions containing 1000, 300, 100 and 10 parts per million (ppm) of 3-t-butyl-1-(dimethylcarbamoyl)-5-(methylthio)pyrazole together with 500 ppm of the wetting agent Lissapol NX were applied to young bean plants, *Viciae fabae*, which were then infested with wingless bean aphids, *Megoura viciae*, sprayed beforehand with the same concentrations of the test solution. The treated plants and insects, together with controls treated with wetting agent alone, were held at 20° C. for 24 hours under cylindrical plastic cages closed at the top with gauze. The percentage mortality of the insects was then recorded. It was found that the treatments at all rates had killed 100% of the test organisms as compared with less than 5% mortality in the controls.

EXAMPLE 22

3-t-butyl-1-(dimethylcarbamoyl)-5-(methylsulphinyl)pyrazole was tested at 1000 ppm in the procedure of Example 21. The treatment killed 100% of the test organisms as compared with less than 5% mortality in the controls.

EXAMPLE 23

1 ml aliquots of acetone solutions of 3-t-butyl-1-(dimethylcarbamoyl)-5-(methylthio)pyrazole were applied to 9 cm diameter filter papers placed in the bottom of 9 cm diameter glass dishes closed by glass lids, at concentrations such as to produce deposits equivalent to 1000, 300, 100 and 30 mg/ft² (mg per 9.3 square dm). The treated surfaces, together with controls treated with acetone alone, were then infested with adult houseflies, *Musca domestica*, and held at 20° C. for 24 hours. The percentage mortality of the insects was then recorded. It was found that the deposits at all rates had killed 100% of the insects as compared with less than 5% mortality in the control treatments.

EXAMPLE 24

1 ml aliquots of acetone solutions of 3-t-butyl-1-dimethylcarbamoyl-5-(methylthio)pyrazole were applied to the inside of glass jars 4.5 cm diameter×9 cms high, closed with a screw cap perforated for ventilation, at concentrations such as to produce deposits equivalent to 50, 15 and 5 mgs/ft² (mg per 9.3 square dm). The treated surfaces, together with controls treated with acetone alone, were then infested with fifth instar nymphs of the German cockroach, *Blattella germanica*, and held at 20° C. for two days. The percentage mortality of the insects was then recorded. It was found that the deposits at all rates had killed 100% of the insects as compared with less than 5% mortality in the control treatments.

EXAMPLE 25

Granules were prepared consisting of:
3-t-butyl-1-dimethylcarbamoyl-5-(methylthio)-pyrazole: 3%
Celatom MP 78 (calcined diatomite granules): 97%

The pyrazole was dissolved in dichloromethane. The resulting solution was added to the Celatom in a concrete mixer. After mixing, the dichloromethane was evaporated off at 35° C.

EXAMPLE 26

A wettable powder was prepared by admixing and then fluid energy milling:
3-t-butyl-7-dimethylcarbamoyl-5-(methylthio)-pyrazole: 25%
Reax 45L (sodium lignin sulphonate): 5%
China clay: 70%

EXAMPLE 27 and 28

The granules of Example 25 were applied evenly along the seed furrows with a glass scoop of the time of sowing sugar beet in plots in fields. The active ingredient was applied at the rate per 100 meters of row shown in the Table. 9 weeks later, the number of the aphids *Aphis fabae* was counted on 15 plants per plot, both on plots containing treated plants and plots containing untreated controls. The mean of 4 replicates was as follows:

| Example | Rate, g per 100 meters | Number of Aphids |
|---|---|---|
| 27 | 70 | 543 |
| 28 | 280 | 533 |
| Control | 0 | 1191 |

EXAMPLES 29–31

The granules of Example 25 were applied onto the soil surface around the base of Brussel sprouts plants, two days after the plants had been transplanted into plots in fields. The rate of active ingredient per plant is shown in Table below. 7 weeks after the treatment, the mean number of the aphids *Brevicoryne brassicae* and *Myzus persicae* per 5 treated, or untreated control, plants were found to be as follows, the figures being the mean of 4 replicates.

| Example | Rate, g per plant | Number of Aphids | |
|---|---|---|---|
| | | B. brassicae | M. persicae |
| 29 | 0.01 | 343.75 | 132.75 |
| 30 | 0.02 | 244.75 | 86.75 |
| 31 | 0.04 | 132.75 | 92.00 |
| Control | 0 | 386.75 | 181.25 |

EXAMPLES 32–34

The granules of Example 25 were scattered round the base of cauliflower plants, two days after the plants had been transplanted into plots in fields. The rate of active ingredient per plant is shown in the Table below. Half the plants were dug up after 7 and 12 weeks, and the percentage root damage index measured as an assessment of cabbage root fly (*Erioischia brassicae*) larval damage. Similar assessment was made of untreated controls. The mean of 4 replicates is shown below:

| Example | Rate, g per plant | Root Damage Index | |
|---|---|---|---|
| | | After 7 weeks | After 12 weeks |
| 32 | 0.01 | 43.27 | 66.53 |
| 33 | 0.02 | 30.48 | 60.52 |
| 34 | 0.04 | 22.59 | 60.84 |
| Control | 0 | 57.48 | 72.04 |

EXAMPLE 35

The wettable powder of Example 26 was admixed with water to produce a suspension containing 0.05% active ingredient. The suspension was sprayed using a carbon dioxide knapsack sprayer at 1200 liters per hectare on to ten Brussels sprouts plants growing in a plot in a field. Before, and one week after, treatment, the number of the caterpillars *Pieris rapae* and *Pieris brassicae* were counted on the 10 plants. Similar assessments were made on untreated controls. The mean results of 3 replicates are shown below:

| Example | Number of Caterpillars | |
|---|---|---|
| | Pre-count | After 1 week |
| 35 | 0.70 | 1.00 |
| Control | 0.79 | 8.70 |

EXAMPLES 36 and 37

The wettable powder of Example 26 was admixed with water to produce a suspension containing the percentage of active ingredient shown in the Table below. The suspension was sprayed at 1000 liters per hectare on to carrot plants growing in plots in fields. Before, 48 hours after, and 1 week after, treatment, counts were made of the number of the aphids *Cavariella aegopodii* on 5 leaves per plot. Similar assessments were made on untreated controls. The mean results of 4 replicates are shown below:

| Example | Dose, % | Number of Aphids | | |
|---|---|---|---|---|
| | | Pre-count | After 48 Hours | After 1 Week |
| 36 | 0.017 | 189.0 | 74.00 | 48.50 |
| 37 | 0.034 | 180.5 | 55.75 | 47.25 |
| Control | 0 | 230.0 | 205.00 | 186.00 |

EXAMPLES 38–40

The wettable powder of Example 26 was admixed with water to produce a suspension containing the percentage of active ingredient shown in the Table below. The suspension was sprayed using a knapsack sprayer at 1250 liters per hectare on to field beans growing in plots in fields. Before treatment the percentage infestation by the aphids *Aphis fabae* was measured, and 48 hours after treatment, the percentage mortality of the same pest was measured, each on 20 plants per plot. Similar assessments were made on untreated controls. The mean results of 4 replicates are shown below.

| Example | Dose, % | % Infestation by Aphids Pre-Count | % Mortality of Aphids 48 Hours after Treatment |
|---|---|---|---|
| 38 | 0.06 | 30 | 100 |

-continued

| Example | Dose, % | % Infestation by Aphids Pre-Count | % Mortality of Aphids 48 Hours after Treatment |
|---|---|---|---|
| 39 | 0.12 | 50 | 100 |
| 40 | 0.24 | 10 | 100 |
| Control | 0 | 20 | 30 |

EXAMPLES 41-43

The wettable powder of Example 26 was admixed with water to produce a suspension containing the percentage of active ingredient shown in the Table below. The suspension was sprayed using a knapsack sprayer at 1300 liters per hectare on to sugar beet growing in plots in fields. Before, and 72 hours after, treatment, the number of the aphids *Myzus persica* and *Aphis fabae* was counted on 20 plants per plot. Similar counts were made on untreated controls. The mean results of 4 replicates are shown below.

| | | Number of Aphids per Plant | | | |
|---|---|---|---|---|---|
| | Dose, | Pre-Count | | 72 hours after Treatment | |
| Example | % | M persica | A fabae | M persica | A fabae |
| 41 | 0.05 | 0.12 | 32.76 | 0 | 0 |
| 42 | 0.11 | 0.25 | 23.85 | 0 | 0 |
| 43 | 0.22 | 0.82 | 38.11 | 0 | 0 |
| Control | 0 | 0.17 | 42.50 | 5.08 | 174.13 |

EXAMPLES 44 AND 45

The wettable powder specified in Example 26 was admixed with water to produce a suspension containing the percentage of active ingredient shown in the Table below. The suspension was sprayed at 1000 liters per hectare on to peach trees growing in plots in fields. Before, and 2, 5 and 6 weeks after treatment, the total number per plot of shoots infested with the aphids *Hyalopterus amygdali* or *Myzus persicae* was counted. Similar assessments were made on untreated controls. The mean results of 5 replicates are shown below.

| | | | Infested Shoots | | |
|---|---|---|---|---|---|
| Example | Dose, % | Pre-Count | After 2 Weeks | After 5 Weeks | After 6 Weeks |
| 44 | 0.05 | 0 | 0 | 0 | 0 |
| 45 | 0.10 | 0 | 0 | 0 | 0 |
| Control | 0 | 0 | 0 | 35 | 700 | — |

We claim:

1. A compound which is a carbamoyl pyrazole of formula

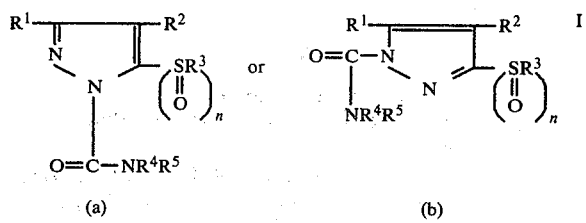

or an acid addition salt thereof, wherein
 $R^1$ represents alkyl of 1-4 carbon atoms;
 $R^2$ represents a hydrogen atom;
 $R^3$ represents alkyl of 1-4 carbon atoms;
 $R^4$ and $R^5$ are the same or different and each represents methyl or ethyl; and
 n represents 0 or 1.

2. A compound according to claim 1 wherein
 $R^1$ represents alkyl of 1-4 carbon atoms; and
 n represents 0.

3. A compound according to claim 1 wherein the alkyl group which $R^1$ represents is branched.

4. A compound according to claim 1 wherein
 $R^1$ represents methyl, isopropyl or t-butyl;
 $R^2$ represents a hydrogen atom;
 $R^3$ represents methyl or ethyl; and
 $R^4$ and $R^5$ each represents methyl or each represents ethyl.

5. A 3-t-butyl-1-(dimethylcarbamoyl)-5-(methylthio)-pyrazole or an acid addition salt thereof.

6. 3-t-butyl-1-(dimethylcarbamoyl)-5-(methylthio)-pyrazole.

7. 3-t-Butyl-1-(dimethylcarbamoyl)-5-(methylsulphinyl)pyrazole or an acid addition salt thereof.

8. A composition effective as an insecticide, acaricide and/or nematocide comprising an effective amount of a compound claimed in claim 1 together with at least one material selected from carriers, surface active agents, or mixtures thereof.

9. A composition according to claim 8 which contains a surface active agent.

10. A composition according to claim 8 which contains, in addition, a material selected from synergists, other pesticides, fertilizers or mixtures thereof.

11. A method of combating insects, acarides and/or nematodes at a locus infested or liable to be infested with them, which method comprises applying to the locus an insect-, acaride- and/or nematode-combating amount of a compound which is a carbamoyl pyrazole of formula

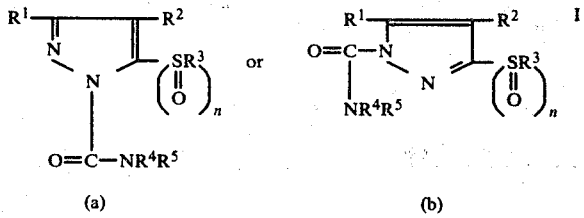

or an acid addition salt thereof, wherein
 $R^1$ represents alkyl of 1-15 carbon atoms or cycloalkyl of 3-6 carbon atoms;
 $R^2$ represents a hydrogen atom or alkyl of 1-6 carbon atoms;
 $R^3$ represents alkyl of 1-15 carbon atoms or alkenyl of 2-6 carbon atoms;
 $R^4$ and $R^5$ are the same or different and each represents alkyl of 1-6 carbon atoms; and
 n represents 0, 1 or 2.

12. A method according to claim 11 wherein plants are growing or are to grow at the locus.

* * * * *